United States Patent [19]

Gangneux

[11] 4,039,545
[45] Aug. 2, 1977

[54] PIGMENTARY IMIDO-PERINONES

[75] Inventor: Philippe Yves Edouard Gangneux, Bihorel, France

[73] Assignee: Produits Chimiques Ugine Kuhlmann, Paris, France

[21] Appl. No.: 589,222

[22] Filed: June 23, 1975

Related U.S. Application Data

[63] Continuation of Ser. No. 330,331, Feb. 7, 1973, abandoned.

[30] Foreign Application Priority Data

Feb. 7, 1972  United Kingdom .............. 03974/72

[51] Int. Cl.² .......................................... C07D 471/22
[52] U.S. Cl. ............................................. 260/256.4 F
[58] Field of Search ................................. 260/256.4 F

[56] References Cited

U.S. PATENT DOCUMENTS 2,225,392  12/1940  Pool et al. ............................ 134/24
3,544,573  12/1970  Christmann ...................... 260/256.4

Primary Examiner—Donald G. Daus
Assistant Examiner—James H. Turnipseed
Attorney, Agent, or Firm—Beveridge, De Grandi, Kline & Lunsford

[57] ABSTRACT

Imido-perinones falling within one of the formulae:

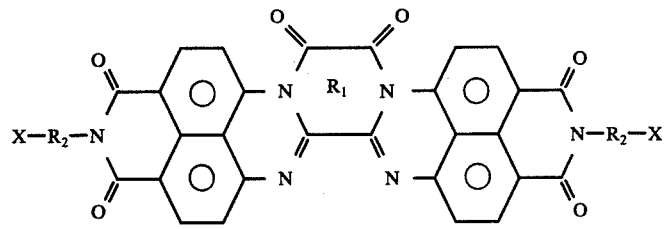

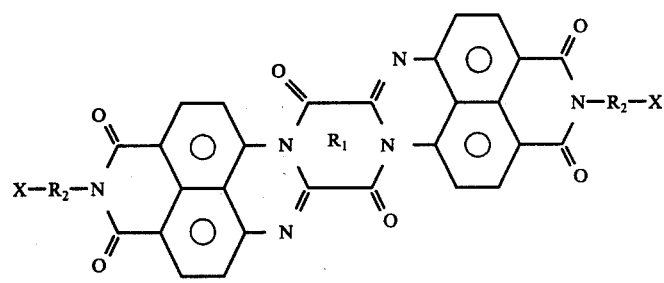

wherein $R_1$ represents the tetravalent residue of a substituted or unsubstituted aromatic hydrocarbon, $R_2$ represents a substituted or unsubstituted aliphatic or aromatic radical and X represents a primary amino, carboxy or hydroxy group, process for the preparation of such imido perinones which comprises condensing a tetracid of the formula:

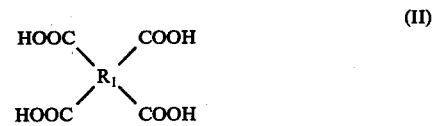

(II)

or the corresponding anhydride with 4,5-diamino-1,8-naphthalic anhydride at the rate of at least two moles of diamine per mole of tetracid and then condensing the perinone dianhydride thus obtained with an amine of the formula:

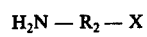

$H_2N - R_2 - X$ wherein $R_1$, $R_2$ and X have the same significance as in claim 1, at the rate of at least two moles of amine, per mole of perinone, and the use of such imido-perinones in the coloration of lacquers, plastic materials or synthetic fibres.

5 Claims, No Drawings

PIGMENTARY IMIDO-PERINONES

This is a continuation, of application Ser. No. 330,331 filed Feb. 7, 1973 now abandoned.

The invention relates to pigmentary imido-perinones, to a process for their preparation and to their use for colouring bulk lacquers, plastic materials and synthetic fibres.

According to the present invention imido-perinones are provided of the following general formulae, which correspond to the cis and trans forms:

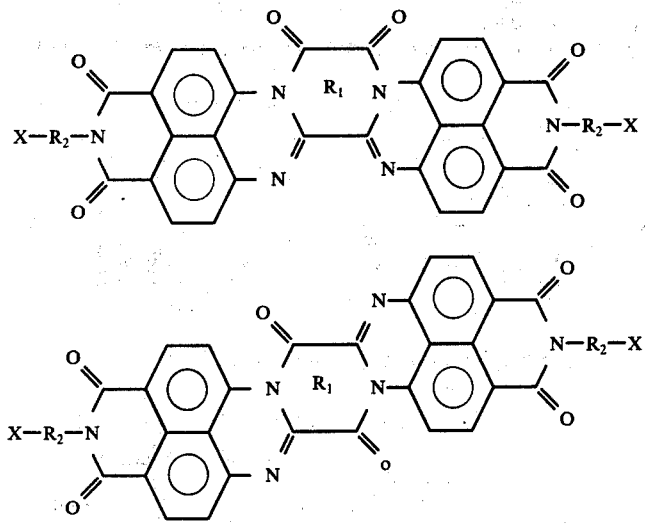

Wherein $R_1$ represents the tetravalent residue of a substituted or unsubstituted benzenic, naphthalenic, anthracenic, phenanthrenic, naphthacenic, or perylenic nucleus or phenylbenzophenone, $R_2$ represents a substituted or unsubstituted aliphatic or aromatic radical and X represents a primary amino, carboxy or hydroxy group.

The substituents of the aromatic residue $R_1$ may be, for example, halogen atoms or nitro, hydroxy or alkoxy groups. The substituents of $R_2$ may be for example halogen atoms or nitro, alkyl or alkoxy groups.

The perinones of formulae Ic and It may be prepared for example by condensing a tetracid of the general formula:

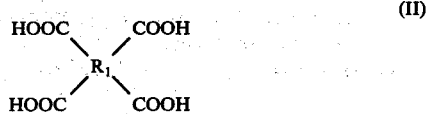

(II)

or corresponding anhydride, with 4,5-diamino-1,8-naphthalic anhydride at the rate of at least two moles of diamine per mole of tetracid and then condensing the perinone dianhydride thus obtained with an amine of the general formula:

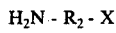

$H_2N - R_2 - X$ wherein $R_1$, $R_2$ and X have the same significance as above, at the rate of at least two, preferably three, moles of amine, per mole of perinone.

According to the invention, the tetravalent residue $R_1$ may be the benzenic, naphthalenic, anthracenic, phenanthrenic, naphthacenic, or perylenic nucleus, or for instance phenylbenzophenone. Aliphatic radicals are those derived from linear hydrocarbons having from 1 to 10 carbon atoms. Preferred alkyl or alkoxy groups are those having from 1 to 5 carbon atoms.

The radical $R_1$ may bear up to 4 substituants, but preferably bears 2 of them, whereas $R_2$ does not comprise more than 2 substituents.

Examples of tetracids and tetracid anhydrides are pyromellitic acid and its anhydride and their derivatives substituted in positions 1 and 4 by halogen atoms or N-alkyl or N-aryl amino groups, 1,4,5,8-naphthalenetetracarboxylic acid and its anhydride, 3,4,9,10-perylenetetracarboxylic acid and its anhydride and their derivatives substituted by halogen atoms or hydroxy, alkyl or alkoxy groups.

The condensations are effected in a solvent medium at temperatures above 150° C and preferably above 200° C. Examples of solvents which may be used are trichlorobenzene, nitrobenzene, or quinoline. Accelerators such as zinc chloride may be added to the reaction medium.

The imido-perinones of formulae Ic and It are blue pigmentary dyestuffs, insoluble in the usual organic solvents, and suitable at high temperature for example, at a temperature higher than 300° C. and possibly higher than 350° C. They are suitable, possibly after grinding to a very finely divided form, for the colouration in bulk of lacquers, plastic materials and synthetic fibres.

In the following Examples which are purely illustrative the parts are parts by weight.

EXAMPLE 1

A mixture comprising 2 parts of 3,4,9,10-perylenetetracarboxylic anhydride, 3 parts of 4,5-diamino-naphthalic anhydride and 0.5 parts of anhydrous zinc chloride in 100 parts of quinoline is heated for 15 hours at 220° C.

After cooling, the product is filtered off, washed with quinoline, the precipitate is taken up in 200 parts of hot methanol, filtered, washed with methanol, then with ethyl ether and dried for 5 hours at 150° C. under vacuum.

A blue product, soluble in sulphuric acid to give a bordeaux shade, which consists of a mixture of the cis and trans imidoazoles, is obtained in good yield.

One part of this product in very finely divided form is condensed with one part of paraphenylenediamine in the presence of 0.2 parts of anhydrous zinc chloride in 100 parts of quinoline. The mixture is heated for 15 hours at 220° C. The precipitate is recovered and is treated like the preceding one. A deep blue dyestuff is obtained which is insoluble in the usual organic solvent, and its melting point is over 400° C.

EXAMPLE 2

One operates as in Example 1, but 1 part of p-aminobenzoic acid is used instead of the paraphenylenediamine.

A deep violet dyestuff is obtained which is insoluble in the usual organic solvents, and its melting point is above 400° C.

EXAMPLE 3

One operates as in Example 1, but one part of hexamethylenediamine is used instead of paraphenylenediamine. A deep blue dyestuff insoluble in the usual organic solvents with a melting point above 400° C. is obtained.

EXAMPLE 4

A mixture comprising 1 part of 1,4,5,8-naphthalenetetracarboxylic anhydride, 3 parts of 4,5-diamino-naphthalic anhydride and 0.5 parts of anhydrous zinc chloride in 90 parts of quinoline is heated for 15 hours at 220° C.

The condensation product is separated as in Example 1. A deep grey product consisting of a mixture of the two cis and trans imidoazole compounds is obtained in good yield.

One part of this product in a very finely divided form is condensed with one part of paraphenylenediamine in the presence of 0.2 parts of anhydrous zinc chloride in 100 parts of quinoline. The mixture is heated for 15 hours at 220° C. and the precipitate is recovered as before.

A deep grey dyestuff insoluble in the usual organic solvents is obtained, of which the melting point is above 400° C.

I claim:

1. A compound of the formulae, having a cis form

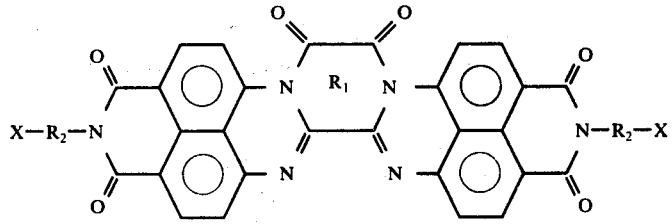

and having a corresponding trans form

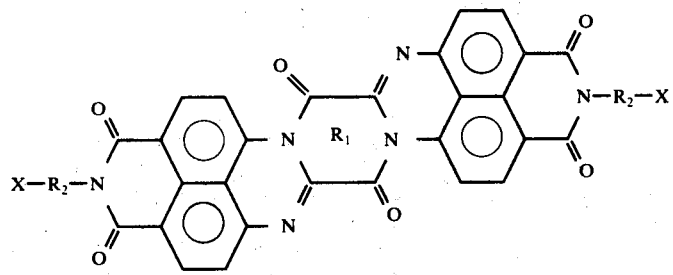

wherein $R_1$ represents unsubstituted benzene 1,2,4,5-tetrayl, naphthalene 1,4,5,8-tetrayl or perylene 3,4,9,10-tetrayl, $R_2$ represents unsubstituted para-phenylene or linear alkylene having from 1 to 10 carbon atoms, and X represents amino or carboxy.

2. Compound according to claim 1 in which $R_1$ is 3, 4, 9, 10 - perylene; $R_2$ is p-phenylene; and X is $NH_2$.

3. Compound according to claim 1 in which $R_1$ is 3, 4, 9, 10 - perylene; $R_2$ is p - phenylene; and X is COOH.

4. Compound according to claim 1 in which $R_1$ is 3, 4, 9, 10 - perylene; $R_2$ is hexamethylene and X is $NH_2$.

5. Compound according to claim 1 in which $R_1$ is 1, 4, 5, 8 - naphthalene; $R_2$ is p - phenylene and X is $NH_2$.

* * * * *

UNITED STATES PATENT AND TRADEMARK OFFICE
CERTIFICATE OF CORRECTION

PATENT NO. : 4,039,545
DATED : August 2, 1977
INVENTOR(S) : Philippe Yves Edouard Gangneux It is certified that error appears in the above-identified patent and that said Letters Patent are hereby corrected as shown below:

Foreign Application Priority Data should read:

Feb. 7, 1972   France ..............03974/72

Signed and Sealed this

Twenty-ninth Day of November 1977

[SEAL]

Attest:

RUTH C. MASON
*Attesting Officer*

LUTRELLE F. PARKER
*Acting Commissioner of Patents and Trademarks*